(12) United States Patent
Wang et al.

(10) Patent No.: US 9,012,145 B2
(45) Date of Patent: *Apr. 21, 2015

(54) PROTEIN TYROSINE PHOSPHATASE MUTATIONS IN CANCERS

(75) Inventors: Zhenghe Wang, Baltimore, MD (US); Victor Velculescu, Dayton, MD (US); Kenneth W. Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 51 days.

This patent is subject to a terminal disclaimer.

(21) Appl. No.: 13/275,958

(22) Filed: Oct. 18, 2011

(65) Prior Publication Data

US 2012/0095086 A1 Apr. 19, 2012

Related U.S. Application Data

(63) Continuation of application No. 11/596,349, filed as application No. PCT/US2005/017105 on May 16, 2005, now Pat. No. 8,039,210.

(60) Provisional application No. 60/571,436, filed on May 14, 2004.

(51) Int. Cl.
  *C12Q 1/68* (2006.01)
  *C12Q 1/42* (2006.01)

(52) U.S. Cl.
  CPC ........ *C12Q 1/6886* (2013.01); *C12Q 2600/136* (2013.01); *C12Q 2600/156* (2013.01)

(58) Field of Classification Search
  CPC ...... C12Q 1/68; C12Q 1/6869; C12Q 1/6886; C12Q 1/6827; C12Q 2600/112; C12Q 2066/118; C12Q 2600/156
  See application file for complete search history.

(56) References Cited

U.S. PATENT DOCUMENTS 7,129,040 B2 10/2006 Steck et al.
7,504,222 B2 3/2009 Ayers et al.

FOREIGN PATENT DOCUMENTS

WO 00/75339 A1 12/2000

OTHER PUBLICATIONS

Campbell et al., Biology, 6th Edition, 2002, p. 322-323.*
Silva et al., Cancer Res., 1999, 59:3251-3256.*
Gross et al., Hum. Genet, 1999, 105:72-78.*
Streuli, et al.: Distinct functional roles of the two intracellular phosphatase like domains of the receptor-linked protein tyrosine phosphatase LCA and LAR, The EMBO Journall, vol. 9, No. 8, pp. 2399-2407, 1990.
Yang, et al.: "Leukocyte Common Antigen-Related Tyrosine Phosphatase Receptor: Increased Expression and Neuronal-Type Splicing in Breast Cancer Cells and Tissue", Molecular Carcinogenesis, 1999, vol. 25, pp. 139-149.
Laforgia, et al.: Receptor protein-tyrosine phosphatase γ is a candidate tumor suppressor gene at human chromosome region 3p21, Proc. Nat'l Acad. Sci., USA, 1991, vol. 88, pp. 5036-5040.
Colozza et al., Annals Oncol., 2005, 16:1723-1739.
Coradini et al., Curr. Opin. Obst. Gyn. 2004, 16:49-55.
Lee et al., APMIS, 2007, 115: 47-51.
Collins, Award No. DAMD17-01-01-0500, US Army Medical Research and Material Command, Aug. 2002.
Andersen et al., FASEB J., Jan. 18, 2004: 8-30.

* cited by examiner

*Primary Examiner* — Hong Sang
(74) *Attorney, Agent, or Firm* — Banner & Witcoff, Ltd.

(57) ABSTRACT

Tyrosine phosphorylation, regulated by protein tyrosine phosphatases (PTPs) and kinases (PTKs), is important in signaling pathways underlying tumorigenesis. A mutational analysis of the tyrosine phosphatase gene superfamily in human cancers identified 83 somatic mutations in six PTPs (PTPRF, PTPRG, PTPRT, PTPN3, PTPN13, PTPN14), affecting 26% of colorectal cancers and a smaller fraction of lung, breast and gastric cancers. Fifteen mutations were nonsense, frameshift or splice site alterations predicted to result in truncated proteins lacking phosphatase activity. Five missense mutations in the most commonly altered PTP (PTPRT) were biochemically examined and found to reduce phosphatase activity. Expression of wild-type but not a mutant PTPRT in human cancer cells inhibited cell growth. These observations suggest that the tyrosine phosphatase genes are tumor suppressor genes, regulating cellular pathways that may be amenable to therapeutic intervention.

21 Claims, 8 Drawing Sheets

Fig. 5

Mutations of the tyrosine phosphatome in human cancers

| Gene | Other names | Accession* | Group | No. of mutations (% tumors affected)# | Tumor type | Tumor | Nucleotide† | Amino Acid† | KRAS / BRAF Mutation** | Tyrosine Kinome Mutation** |
|---|---|---|---|---|---|---|---|---|---|---|
| *PTPRT* | RPTPrho | NM_133170 hCT1955988 | RPTP | 27 (11%) colorectal cancers | colorectal | Hx184 | G625A / G3805A | A209T / V1269M | KRAS | none |
| | | | | | colorectal | Co86 | G625A | A209T | KRAS | none |
| | | | | | colorectal | Hx29 | T743C | F248S | ND | MLK4 |
| | | | | | colorectal | Hx138 | T838C | Y280H | KRAS | none |
| | | | | | colorectal | Co76 | A1235T | Y412F | none | none |
| | | | | | colorectal | Hx113 | T1530G | N510K | BRAF | none |
| | | | | | colorectal | Co61 | C1814T | T605M | BRAF | none |
| | | | | | colorectal | Hx48 | T1943G | V648G | KRAS | none |
| | | | | | colorectal | Hx101 | C1894T / 3280del | R632X / frameshift | BRAF | none |
| | | | | | colorectal | Co80 | G2119A / A2780G | A707T / Q927G | none | MLK4, GUCY2F |
| | | | | | colorectal | Co83 | C2120T / C3061T | A707V / R1021X | KRAS | none |
| | | | | | colorectal | Hx124 | T221C / T2123C | F74S / L708P | ND | GUCY2F |
| | | | | | colorectal | Co27 | C2923T / LOH | R975X / LOH | none | none |
| | | | | | colorectal | Hx150 | C2999A | Q987K | KRAS | none |
| | | | | | colorectal | Hx63 | G3352C / C4103T | A1118P / T1368M | KRAS | none |
| | | | | | colorectal | Hx125 | A3383T | N1128I | ND | none |
| | | | | | colorectal | Hx12 | C3634T | R1212W | KRAS | none |
| | | | | | colorectal | Hx143 | A3775T | M1259L | KRAS | none |
| | | | | | colorectal | Hx138 | A1183G / A4052T | I395V / Y1351F | KRAS | none |
| | | | | | colorectal | Hx64 | C4103T | T1368M | KRAS | ND |
| | | | | 2 (17%) gastric cancers | gastric | G8 | C1357T | R453C | ND | ND |
| | | | | | gastric | G10 | A653C | K218T | ND | ND |
| | | | | 2 (33%) lung cancers | lung | L7 | G4037T | R1346L | ND | ND |
| | | | | | lung | L9 | C2368T | R790X | ND | ND |
| *PTPRG* | PTPG HPTPG RPTPG R-PTP-gamma | NM_002841 hCT14049 | RPTP | 4 (5%) colorectal cancers | colorectal | Mx9 | C1082T | T361M | KRAS | none |
| | | | | | colorectal | Cx10 | C1385T | A462V | KRAS | none |
| | | | | | colorectal | Co69 | C1541T | T514M | none | none |
| | | | | | colorectal | Hx101 | C1777T | R593W | BRAF | none |

Table S2. Tyrosine phosphatome genes analyzed

| Celera Accession | Genbank Accession | Gene Name | Gene Description | Family |
|---|---|---|---|---|
| hCT6568 | NM_032781.2 | PTPN5 | protein tyrosine phosphatase, non-receptor type 5 | PTP |
| hCT6451 | NM_015466.1 | PTPN23 | protein tyrosine phosphatase, non-receptor type 23 (HD-PTP) | PTP |
| hCT1950416 | NM_016364.2 | DUSP13 | dual specificity phosphatase 13 | DSP |
| hCT32908 | NM_021090.2 | MTMR3 | myotubularin related protein 3 | PTP |
| hCT32877 | NM_003479.2 | PTP4A2 | protein tyrosine phosphatase type IVA, member 2 | PTP |
| hCT18420 | NM_130391.1 | PTPRD | protein tyrosine phosphatase, receptor type, D | PTP |
| hCT1822630 | NM_177995.1 | PTP9Q22 | protein tyrosine phosphatase PTP9Q22 | PTP |
| hCT30485 | NM_000252.1 | MTM1 | myotubular myopathy 1 | PTP |
| hCT1951990 | NM_001395.1 | DUSP9 | dual specificity phosphatase 9 | DSP |
| hCT1815053 | NM_080876.2 | DUSP19 | dual specificity phosphatase 19 (DUSP19) | DSP |
| hCT32625 | NM_016086.2 | MK-STYX | map kinase phosphatase-like protein MK-STYX | DSP |
| hCT1962353 | NM_080683 | PTPN13 | protein tyrosine phosphatase, non-receptor type 13 (FAP1) | PTP |
| hCT32515 | NM_004417.2 | DUSP1 | dual specificity phosphatase 1 | DSP |
| hCT1644566 | XM_062330 | | similar to protein tyrosine phosphatase, receptor, type, Q | PTP |
| hCT1644559 | XM_291741 | | similar to Dual specificity protein phosphatase 13 | DSP |
| hCT17069 | NM_002831.3 | PTPN6 | protein tyrosine phosphatase, non-receptor type 6 (SHP1) | PTP |
| hCT24042 | NM_003672.2 | CDC14A | CDC14 cell division cycle 14 homolog A | DSP |
| hCT1970499 | NM_080422.1 | PTPN2 | protein tyrosine phosphatase, non-receptor type 2 (TCPTP) | PTP |
| hCT1774420 | NM_033331.1 | CDC14B | CDC14 cell division cycle 14 homolog B | DSP |
| hCT16535 | NM_002849.2 | PTPRR | protein tyrosine phosphatase, receptor type, R | PTP |
| hCT1813286 | NM_004685.1 | MTMR6 | myotubularin related protein 6 | PTP |
| hCT28528 | NM_004418.2 | DUSP2 | dual specificity phosphatase 2 | DSP |
| hCT16333 | NM_002840 | PTPRF | protein tyrosine phosphatase, receptor type, F (LAR) | PTP |
| hCT9118 | NM_005670.2 | EPM2A | epilepsy, progressive myoclonus type 2A | DSP |
| hCT1955131 | NM_022648.2 | TNS | tensin | PTP |
| hCT28429 | NM_002828.2 | PTPN2 | protein tyrosine phosphatase, non-receptor type 2 | PTP |
| hCT1813194 | NM_030667.1 | PTPRO | protein tyrosine phosphatase, receptor type, O | PTP |
| hCT28364 | NM_002827.2 | PTPN1 | protein tyrosine phosphatase, non-receptor type 1 (PTP1b) | PTP |
| hCT16271 | NM_002837.2 | PTPRB | protein tyrosine phosphatase, receptor type, B | PTP |
| hCT1953979 | NM_133178.1 | PTPRU | protein tyrosine phosphatase, receptor type, U | PTP |
| hCT16153 | NM_007207.3 | DUSP10 | dual specificity phosphatase 10 | DSP |
| hCT1953703 | XM_294600 | | protein tyrosine phosphatase, receptor type, W (LOC347319) | PTP |
| hCT1788895 | NM_002833.2 | PTPN9 | protein tyrosine phosphatase, non-receptor type 9 (MEG2) | PTP |
| hCT11101 | NM_007039.2 | PTPN21 | protein tyrosine phosphatase, non-receptor type 21 (PTPH1) | PTP |
| hCT1797443 | NM_003463.2 | PTP4A1 | protein tyrosine phosphatase type IVA, member 1 | PTP |
| hCT14949 | NM_002841 | PTPRG | protein tyrosine phosphatase, receptor type, G | PTP |
| hCT14765 | AB033100 | | mRNA for KIAA1274 protein | PTP |
| hCT1951768 | NM_002838.2 | PTPRC | protein tyrosine phosphatase, receptor type, C (CD45) | PTP |
| hCT1951740 | NM_004419.2 | DUSP5 | dual specificity phosphatase 5 | DSP |
| hCT14606 | NM_002850.2 | PTPRS | protein tyrosine phosphatase, receptor type, S | PTP |
| hCT1816300 | NM_152511.2 | DUSP18 | dual specificity phosphatase 18 | DSP |
| hCT33868 | XM_037430 | DUSP7 | dual specificity phosphatase 7 | DSP |
| hCT1950123 | NM_007026.1 | DUSP14 | dual specificity phosphatase 14 | DSP |
| hCT14332 | NM_002843.2 | PTPRJ | protein tyrosine phosphatase, receptor type, J | PTP |
| hCT11067 | NM_002844.2 | PTPRK | protein tyrosine phosphatase, receptor type, K | PTP |
| hCT21458 | NM_004090.1 | DUSP3 | dual specificity phosphatase 3 | DSP |
| hCT1823204 | NM_004420.1 | DUSP8 | dual specificity phosphatase 8 | DSP |
| hCT30064 | NM_177991.1 | DUSP15 | dual specificity phosphatase-like 15 | DSP |
| hCT10729 | NM_002842.1 | PTPRH | protein tyrosine phosphatase, receptor type, H | PTP |
| hCT1640496 | NM_003828.1 | MTMR1 | myotubularin related protein 1 | PTP |
| hCT1961579 | NM_024025.1 | MGC1136 | hypothetical protein MGC1136 | DSP |
| hCT1645239 | NM_015605.2 | DKFZP566K0524 | DKFZP566K0524 protein | PTP |
| hCT1788024 | NM_022076.2 | DUSP21 | dual specificity phosphatase 21 | DSP |
| hCT1787727 | NM_015967.2 | PTPN22 | protein tyrosine phosphatase, non-receptor type 22 (LyP1) | PTP |
| hCT32220 | NM_130435.1 | PTPRE | protein tyrosine phosphatase, receptor type, E | PTP |
| hCT17735 | NM_001946.1 | DUSP6 | dual specificity phosphatase 6 | DSP |
| hCT1640270 | NM_004090.1 | DUSP3 | dual specificity phosphatase 3 | DSP |
| hCT30758 | NM_003584.1 | DUSP11 | dual specificity phosphatase 11 | DSP |
| hCT1640130 | XM_043739 | | hypothetical cardiac/skeletal muscle-expressed ORF | DSP |
| hCT31884 | NM_002835.2 | PTPN12 | protein tyrosine phosphatase, non-receptor type 12 (PTP-PEST) | PTP |
| hCT12542 | NM_016156.2 | MTMR2 | myotubularin related protein 2 | PTP |
| hCT24607 | NM_002851.1 | PTPRZ1 | protein tyrosine phosphatase, receptor-type, Z polypeptide 1 | PTP |
| hCT1686528 | NM_002845.2 | PTPRM | protein tyrosine phosphatase, receptor type, M | PTP |
| hCT12147 | NM_017857.2 | SSH-3 | slingshot 3 | DSP |
| hCT12099 | NM_002836.2 | PTPRA | protein tyrosine phosphatase, receptor type, A | PTP |
| hCT31320 | NM_001585.2 | C22orf1 | chromosome 22 open reading frame 1 | PTP |
| hCT1963526 | NM_017677.2 | MTMR8 | myotubularin related protein 8 | PTP |
| hCT1820965 | NM_002834.3 | PTPN11 | protein tyrosine phosphatase, non-receptor type 11 (Noonan syndrome 1) (SHP2) | PTP |
| hCT1766350 | NG_001337.1 | | T cell receptor beta variable orphans on chromosome 9 | PTP |
| hCT1805295 | NM_017823.2 | FLJ20442 | hypothetical protein FLJ20442 | PTP |
| hCT22967 | NM_002832.2 | PTPN7 | protein tyrosine phosphatase, non-receptor type 7 | PTP |
| hCT1964913 | NM_057158.2 | DUSP4 | dual specificity phosphatase 4 (Typ) | DSP |
| hCT1957126 | NM_002830.2 | PTPN4 | protein tyrosine phosphatase, non-receptor type 4 (MEG1) | PTP |
| hCT1955989 | NM_133170 | PTPRT | protein tyrosine phosphatase, receptor type, T | PTP |
| hCT20252 | NM_033389.1 | SSH2 | slingshot 2 | DSP |
| hCT6880 | NM_007240.1 | DUSP12 | dual specificity phosphatase 12 | DSP |
| hCT18898 | NM_017677.2 | MTMR8 | myotubularin related protein 8 | PTP |
| hCT6725 | NM_018984.1 | SSH1 | slingshot 1 | DSP |
| hCT1958113 | NM_002829.2 | PTPN3 | protein tyrosine phosphatase, non-receptor type 3 (PTPH1) | PTP |
| hCT6590 | NM_002846.2 | PTPRN | protein tyrosine phosphatase, receptor type, N | PTP |
| hCT9393 | NM_001789 | CDC25A | cell division cycle 25A | DSP |
| hCT2254822 | NM_022809 | CDC25C | cell division cycle 25C | DSP |
| hCT1951353 | NM_021874 | CDC25B | cell division cycle 25B | DSP |
| hCT2270543 | NM_014369 | PTPN18 | protein tyrosine phosphatase, non-receptor type 18 | PTP |
| hCT2261290 | NM_005401 | PTPN14 | protein tyrosine phosphatase, non-receptor type 14 | PTP |
| hCT2287788 | NM_007099 | ACP1 | acid phosphatase 1 | LMP |
| hCT1641130 | NM_145251.2 | STYX | serine/threonine/tyrosine interacting protein | DSP |

PROTEIN TYROSINE PHOSPHATASE MUTATIONS IN CANCERS

This invention was made under contracts (CA43460 and CA63934) with an agency (National Institutes of Health) of the United States Government. The United States Government therefore retains certain rights in the invention.

This application incorporates a 502 KB text file named "seqlst00631" created Jul. 22, 2010, which is the sequence listing for this application.

TECHNICAL FIELD OF THE INVENTION

This invention is related to the area of cancer. In particular, it relates to diagnosis, prognosis, treatment, drug discovery, target discovery, clinical testing for cancer.

BACKGROUND OF THE INVENTION

Phosphorylation of tyrosine residues is a central feature of most cellular signaling pathways, including those affecting growth, differentiation, cell cycle regulation, apoptosis and invasion (1, 2). This phosphorylation is coordinately controlled by protein tyrosine kinases (PTKs) and phosphatases (PTPs). Although a variety of PTK genes have been directly linked to tumorigenesis through somatic activating mutations (3-6) only a few PTP genes have been implicated in cancer (7-10). Moreover, it is not known how many or how frequently members of the PTP gene family are altered in any particular cancer type.

The PTP gene superfamily is composed of three main families: (i) the classical PTPs, including the receptor PTPs (RPTPs) and the non-receptor PTPs (NRPTPs); (ii) the dual specificity phosphatases (DSPs), which can dephosphorylate serine and threonine in addition to tyrosine residues; and (iii) the low molecular weight phosphatases (LMPs) (1).

There is a continuing need in the art to identify new therapeutic targets, identify new drugs, improve diagnosis, prognosis, and therapy of cancers.

SUMMARY OF THE INVENTION

One aspect of the invention is a method for identifying mutations involved in cancer. Nucleotide sequence differences are determined in a human nucleotide sequence between matched pairs of cancer cells and normal cells. Each matched pair of cells is isolated from a single individual. The human nucleotide sequence encodes a protein tyrosine phosphatase selected from the group consisting of: PTPRF, PTPRG, PTPRT, PTPN3, PTPN13, and PTPN14.

Another aspect of the invention is a method of screening test substances for use as anti-cancer agents. A test substance is contacted with a wild-type form of a protein tyrosine phosphatase or a mutant form of a protein tyrosine phosphatase which is mutated in cancer cells. Activity of the form of the protein tyrosine phosphatase is tested. A test substance which increases the activity of the form of a protein tyrosine phosphatase is a potential anti-cancer agent. The protein tyrosine phosphatase is selected from the group consisting of: PTPRF, PTPRG, PTPRT, PTPN3, PTPN13, and PTPN14.

One embodiment of the invention provides an isolated, mutant form of a protein tyrosine phosphatase. The phosphatase is selected from the group consisting of: PTPRF, PTPRG, PTPRT, PTPN3, PTPN13, and PTPN14. Enzymatic activity of the mutant form is reduced compared to wild-type.

Another embodiment of the invention provides an isolated polynucleotide which encodes a mutant form of protein tyrosine phosphatase. The phosphatase is selected from the group consisting of: PTPRF, PTPRG, PTPRT, PTPN3, PTPN13, and PTPN14. Enzymatic activity of the mutant form is reduced compared to wild-type.

Still another aspect of the invention is a method of categorizing cancers. The coding sequence for or the amino acid sequence of one or more protein tyrosine phosphatase family members in a sample of a cancer tissue is determined. The family member is selected from the group consisting of PTPRF, PTPRG, PTPRT, PTPN3, PTPN13, and PTPN14.

A somatic mutation of the one or more protein tyrosine phosphatase family members is identified in the cancer tissue. The cancer tissue is assigned to a group based on the presence or absence of the somatic mutation.

According to another aspect of the invention a method of inhibiting growth of cancer cells is provided. A polynucleotide encoding a wild-type protein tyrosine phosphatase is administered to cancer cells. The phosphatase is selected from the group consisting of PTPRF, PTPRG, PTPRT, PTPN3, PTPN13, and PTPN14, Growth of the cancer cells is thereby inhibited.

Yet another aspect of the invention is a method of identifying cancer cells in a sample collected from a human. The coding sequence for or the amino acid sequence of one or more protein tyrosine phosphatase family members in a sample collected from the human is determined. The family member is selected from the group consisting of PTPRF, PTPRG, PTPRT, PTPN3, PTPN13, and PTPN14. The sample is selected from the group consisting of a suspected cancer tissue, blood, serum, plasma, and stool. A somatic mutation of said one or more protein tyrosine phosphatase family members is identified in the cancer tissue. The sample is identified as containing cancer cells if a somatic mutation is identified.

These and other embodiments which will be apparent to those of skill in the art upon reading the specification provide the art with reagents and methods for detection, diagnosis, therapy, and drug screening pertaining to cancers.

BRIEF DESCRIPTION OF THE DRAWINGS

(FIG. 2A) Saturation kinetics of wild-type and mutant PTPRT. His-tagged versions of PTPRT protein segments comprising the two catalytic domains containing wild-type (WT) and tumor-specific mutant sequences were expressed in bacteria and purified using nickel affinity chromatography. Equal amounts of WT and mutant proteins were used to evaluate enzyme kinetics. The rate of hydrolysis of substrate (DiFMUP) is plotted against increasing substrate concentration. Data were fitted to the Michaelis-Menton equation and the resulting kinetic parameters of WT and mutant proteins are indicated (FIG. 2B).

(FIG. 3A) HCT116 colorectal cancer cells were transfected with wild-type (WT) PTPRT construct, truncated R632X mutant PTPRT construct, or empty pCI-Neo vector. The photographs show colonies stained with crystal violet after 14 days of geneticin selection. (FIG. 3B) Number of resistant colonies (mean of two 25 cm² flasks) for WT PTPRT, mutant PTPRT, and empty vector.

FIG. 5. (Table S1.) Mutations of the tyrosine phosphatome in human cancers

FIG. 6. (Table S2.) Tyrosine phosphatome genes analyzed (SEQ ID NO: 15-101; encoded amino acids SEQ ID NO: 102-187).

DETAILED DESCRIPTION OF THE INVENTION

Figure 1:
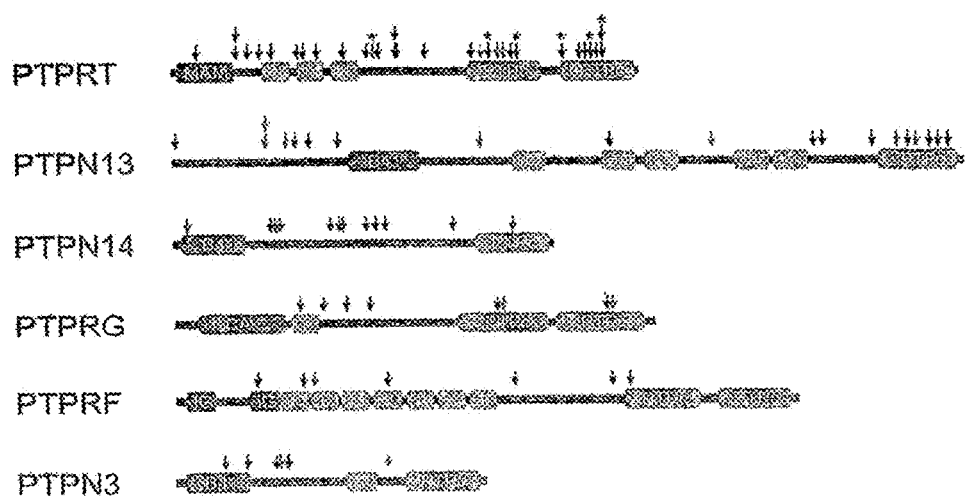
FIG. 1. Distribution of mutations in PTPRT, PTPN13, PTPN14, PTPRG, PTPRF, and PTPN3. Black arrows indicate location of missense mutations, red arrows indicate location of nonsense mutations or frameshifts, and boxes represent functional domains (B41, band 41; CA, carbonic anhydrase; FN3, fibronectin type III; IG, immunoglobulin; MAM, meprin/A5/PTPµ; PDZ, postsynaptic density, discs large, zonula occludans; PTPc, catalytic phosphatase domain). Black stars indicate PTPRT mutants evaluated for phosphatase activity (see results in FIG. 2), and red star indicates PTPRT mutant evaluated for effects on cell proliferation (see results in FIG. 3).

The inventors have discovered that protein tyrosine phosphatase genes are the targets of somatic mutations in cancers, suggesting that these genes function as tumor suppressors in human cells. 87 genes were identified as being members of the protein tyrosine phosphatase superfamily. These include members of the (i) the classical PTPs, (ii) the dual specificity phosphatases (DSPs), and (iii) the low molecular weight phosphatases (LMPs). See FIG. 6. Screening a collection of colorectal cancers identified six different genes of the classical PTPs which are the object of somatic mutations in the colorectal cancers. Some of these genes are also the subject of somatic mutations in breast, lung, and/or gastric cancers. Screening collections of other types of cancers will undoubtedly uncover other sets of the superfamily which are somatically mutated. Other types of cancers which can be screened for mutations include: bladder, melanoma, breast, non-Hodgkin's lymphoma, pancreatic, endometrial, prostate, kidney, skin, leukemia, thyroid, and lung.

Phosphatases which can be screened can be chosen from those shown in FIG. 6. Other phosphatases may be identified for screening, for example, using different bioinformatics criteria as described below. The primers identified below for amplification and sequencing of the phosphatases can be used, or other primers can be used as is convenient for the practitioner. For identification of mutations, determined sequences in samples can be compared to known sequences in the literature. For example, for each of the 87 phosphatases of FIG. 6, a GenBank and a Celera accession number are provided. Sequences determined in samples can be compared to the wild-type sequences provided in the databases and attached sequence listing. However, a better indication of involvement in cancer is provided by comparing a determined sequence to that in a normal tissue of the same human. Such a comparison indicates that a change is a somatic mutation. Sequences in databases refer to the sequences that existed in the databases as of May 14, 2004. GenBank stores and records sequences according to the dates on which they were indicated as the most recent update. Thus the sequences available on May 14, 2004 are maintained and publicly available. See also the sequence listing. It is well recognized in the art that there is variation in the human population of wild-type protein and nucleic acid sequences. Such variation typically maintains sequences within a 95% identity range, more typically within a 97% identity range, and more typically within a 99% identity range.

Matched pairs of cells for determining somatic mutations ideally are cells from a single individual. Typically the cells are of the same type, e.g., lung cancer cells and normal lung cells. If a body sample such as blood or stool is being examined, then normal cells can be selected from any body tissue as a comparator.

Mutations that are relevant to cancer can be in almost any region of the phosphatases, because the relevant mutations are loss-of-function mutations. Thus the mutations can be in the catalytic domain or in other portions of the protein. Mutations can also be in non-coding, regulatory regions of the gene. Non-synonymous mutations change the encoded amino acids of a protein. Thus such mutations are highly likely to be functionally relevant to cancer. Mutations in residues that are evolutionarily conserved among species are also highly likely to be functionally relevant to cancer.

Figure 5:
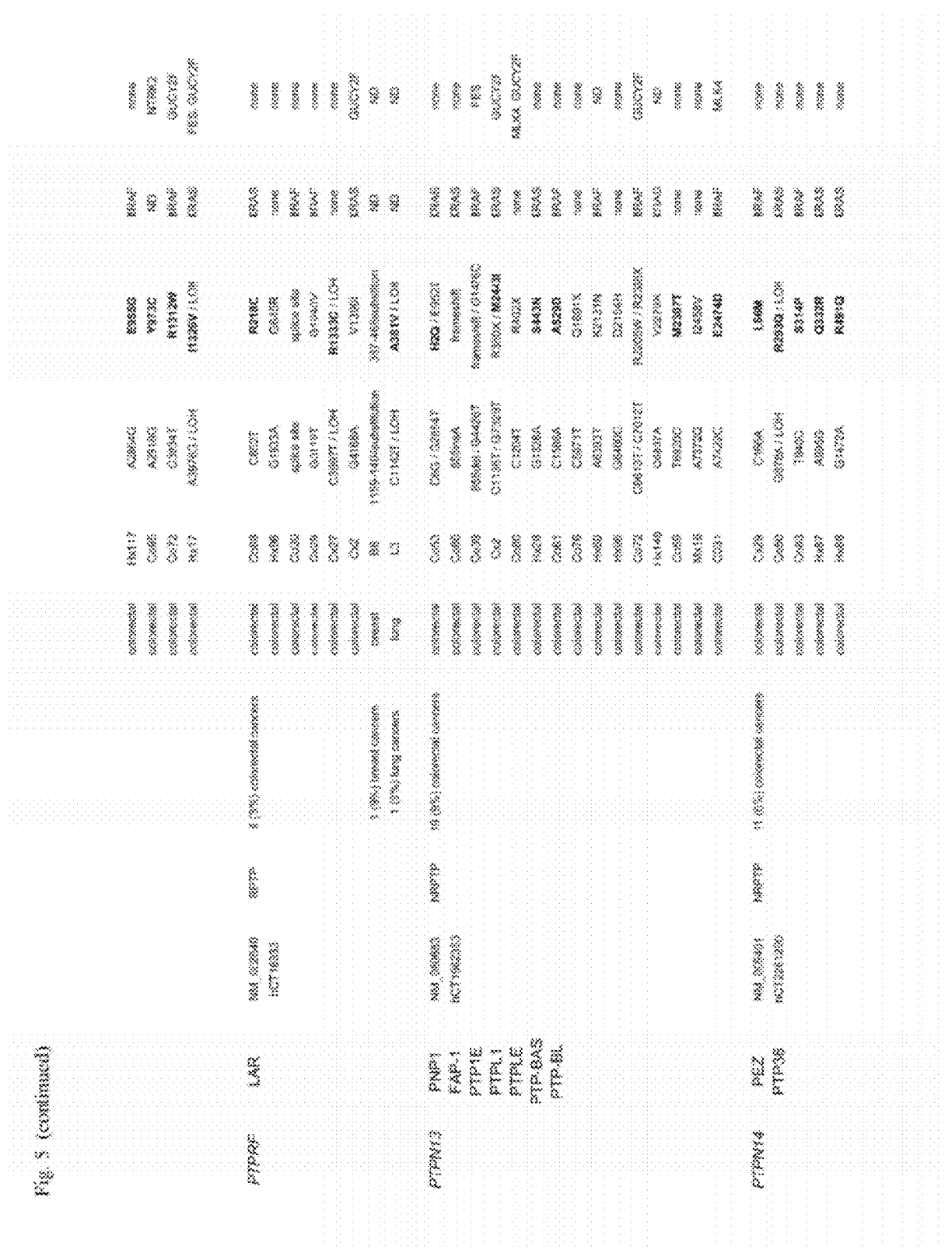
Figure 5:
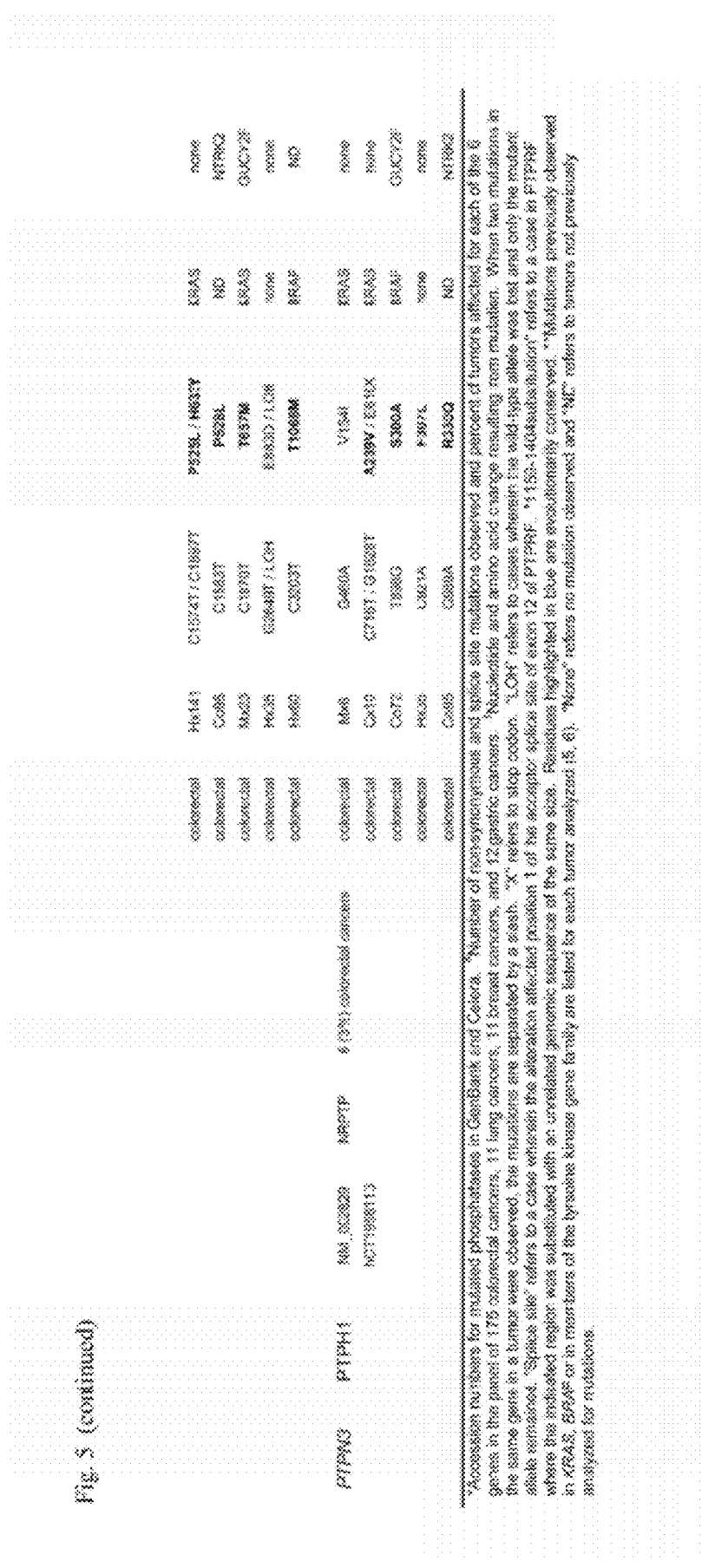

Since loss of protein tyrosine phosphatase activity appears to be detrimental to cells, reacquisition of activity should have a positive, therapeutic effect. Test substances can be tested for their ability to enhance the activity of PTPs by contacting a wild-type or mutant PTP with a test substance. The PTP can be isolated from cells and contacted in a cell-free system, or the PTP may be in cells, either genetically engineered host cells or native cells which express the PTP. The cells can be tested in culture or in a model non-human animal system. Typically the cells will be somatic cells. The PTP can be any mutant or wild-type form, especially one of the six PTPs identified as mutant in colorectal cancers, but also may any of the 87 identified below. One of the mutant forms identified in the present study can be used (see FIG. 5) or other mutant forms, for example those found in other types of cancer. PTPs can be isolated from producing host cells or native producer cells. One means of purifying a PTP is disclosed in example 7, in which a His tag is added to the PTP by cloning and then used to purify the PTP using nickel affinity beads. A desirable test substance for becoming a candidate anti-cancer agent will enhance the activity of a wild-type and/or mutant PTP or enhance PTP activity of a cell with wild-type, mutant, or both types of PTP.

Polynucleotides comprising coding sequences for PTPs, in particular mutant PTPs found in cancer cells, can be naturally occurring coding sequences or coding sequences which are synthesized based on the genetic code and the amino acid sequence of a mutant PTP. The coding sequences can be inserted in expression vectors so that quantities of the mutant PTPs can be produced efficiently and used in drug screening assays. Alternatively, host cells which contain expression vectors encoding mutant PTPs can be used for drug screening assays. The mutant PTPs may be reduced in enzyme activity, for example with a higher $K_m$ or with a lower $K_{cat}$ than wild-type. The mutant PTPs may alternatively have no detectable enzymatic activity.

Isolated polynucleotides are polynucleotides which are separated from the chromosome upon which they normally reside in the human genome. They are typically separated from the genes which flank them on a normal human chromosome. They may be in a vector with an origin of replication, or they may simply be an isolated linear piece of nucleic acid. The polynucleotides encoding PTPs may or may not contain the introns which are present in the human genome.

Cancer tissues can be categorized on the basis of which, if any, phosphatase mutation(s) they contain. Any of the PTPs demonstrated to harbor cancer-related mutations can be used for the categorization. Somatic mutations are identified on the basis of a difference between an affected tissue and a normal tissue of the same individual. Categorization of the tissue can be used for stratifying patients for clinical trials, for analyzing data from clinical trials, for correlating with prognostic data (such as recurrence, metastasis, and life expectancy), as well as for selecting an appropriate course of treatment for a cancer patient. The PTP categorization can be used in conjunction with other data, for example, histopathological data, to identify a cancer. Similarly, PTP somatic mutation analysis can be used in any tissue or body sample to diagnose cancer. Presence of a mutant PTP or coding sequence in a tissue or body sample indicates the presence of cancer cells, either in the sample itself, or in a tissue which drains into the sample. Thus, for example, detection of PTP mutants in a fecal sample reflects the presence of colorectal cancer cells in the human from whom the sample was taken. Body samples which can be tested include without limitation suspected cancerous tissues, stool, sputum, tears, saliva, blood, plasma, serum, urine, and bronchoalveolar lavage.

The mutational data associating loss of PTP function with cancers strongly suggests that PTPs are tumor suppressors. Therefore wild-type PTP coding sequences can be used as therapeutic agents for treating tumors. Wild-type PTP coding sequences are shown in the sequence listing. These sequences or wild-type sequences which are at least 95% identical, at least 96% identical, at least 97% identical, at least 98% identical, or least 99% identical, can be used to deliver wild-type PTP to tumor cells. The coding sequences may or may not contain introns. Sequences for any of the six PTPs identified as somatically mutated in colorectal cancers may be used, as well as any of the other PTPs identified in FIG. 6.

Viral or non-viral vectors may be used for delivery of polynucleotides. For example, adenoviruses, adeno-associated viruses, herpes viruses, and retroviruses can be used for delivery. Non-viral vectors include liposomes, nanoparticles and other polymeric particles. Any vectors or techniques known in the art may be used for delivering genes to cells or humans. See, e.g., *Gene Therapy Protocols*, Paul D. Robbins, ed., Human Press, Totowa, N.J., 1997. Vectors may not be necessary according to some protocols, and coding sequences can be administered without a means of replication. Administration of gene therapy vectors can be by any means known in the art, including but not limited to intravenous, intramuscular, intratumoral, intranasal, intrabronchial, and subcutaneous injections or administration. An effective amount of polynucleotide is one which inhibits growth of cancer cells in a measurable amount. Preferably the tumor regresses and shrinks, or at least ceases to grow larger.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Identification of PTP Gene Superfamily Members

We employed a combination of Hidden Markov Models representing catalytic domains of members of the PTP superfamily to identify 53 classical PTPs (21 RPTPs and 32 NRPTPs), 33 DSPs, and one LMP in the human genome (12). This analysis revealed a set of genes representing all known human PTPs (13) as well as seven putative PTPs.

Example 2

Identification of PTP Gene Superfamily Members with Mutations

As an initial screen to evaluate whether these phosphatases are genetically altered in human cancer, we analyzed the coding exons of all 87 members of this gene family in 18 colorectal cancers. A total of 1375 exons from all annotated RPTPs, NRPTPs, DSPs and LMPs were extracted from genomic databases (12). These exons were PCR-amplified from cancer genomic DNA samples and directly sequenced using dye terminator chemistry (12). Whenever a presumptive mutation was identified, we attempted to determine whether it was somatically acquired (i.e., tumor specific) by examining the sequence of the gene in genomic DNA from normal tissue of the relevant patient.

From the 3.3 Mb of sequence information obtained, we identified six genes containing somatic mutations, including three members of the RPTP subfamily (PTPRF, PTPRG, and PTPRT) and three members of the NRPTP subfamily (PTPN3, PTPN13 and PTPN14). These six genes were then further analyzed for mutations in another 157 colorectal cancers. Through this strategy we identified 77 mutations in the six genes, in aggregate affecting 26% of the colorectal tumors analyzed (Table S1, FIG. 1). Examination of these six genes in seven other tumor types identified PTPRT mutations in two of 11 (18%) lung cancers and two of 12 gastric cancers (17%), and PTPRF mutations in one of 11 (9%) lung cancers and one of 11 (9%) breast cancers. No mutations were identified in 12 pancreatic cancers, 12 ovarian cancers, 12 medulloblastomas or 12 glioblastomas (FIG. 5 (Table S1), FIG. 1). In total, 83 nonsynonymous mutations were observed, all of which were somatic in the cancers that could be assessed (12).

Fifteen of the 83 mutations were nonsense, frameshift or splice site alterations, all of which were predicted to result in aberrant or truncated proteins. In 16 tumors both alleles of the phosphatase gene appeared to be mutated, a characteristic often associated with tumor suppressor genes. The majority of tumors with PTP gene mutations also contained mutations in KRAS or BRAF, and nine tumors contained alterations in previously reported tyrosine kinase genes (FIG. 5 (Table S1)). Thus the mutant phosphatases identified in this study are likely to operate through cellular pathways distinct from those associated with previously identified mutant kinases.

Example 3

Analysis of Mutation Types

Analysis of mutations in tumors is complicated by the fact that mutations can arise either as functional alterations affecting key genes underlying the neoplastic process or as nonfunctional "passenger" changes. The multiple waves of clonal expansion and selection that occur throughout tumorigenesis lead to fixation of any mutation that had previously occurred in any predecessor cell, regardless of whether the mutation was actually responsible for the clonal expansion. Two independent lines of evidence suggest that the sequence alterations we observed are functional. First, the ratio of nonsynonymous to synonymous mutations provides an indication of selection, as synonymous alterations usually do not exert a growth advantage. There were no somatic synonymous mutations detected in the colorectal cancers analyzed, resulting in a ratio of nonsynonymous to synonymous mutations of 77 to 0, much higher than the expected 2:1 ratio for non-selected passenger mutations ($p<1\times10-6$). Second, the prevalence of mutations in the coding regions of the analyzed genes was ~19 per Mb of tumor DNA, similar to the prevalence of functional somatic alterations observed in other gene families (e.g., the tyrosine kinome (6)) and significantly higher than the prevalence of nonfunctional alterations previously observed in the cancer genomes (~1 per Mb, $p<0.01$)

(14). These data support the idea that these mutations were the targets of selection during tumorigenesis.

Example 4

Effect of Point Mutations on Enzymatic Activity

Figure 2A:
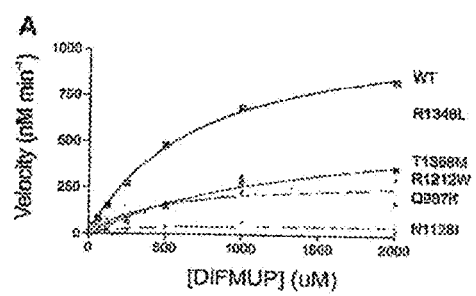
FIG. 2A-2B. Evaluation of phosphatase activity of mutant PTPRT.
Figure 2B:
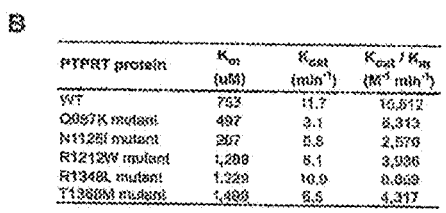

The great majority of the nonsense and frameshift mutations (FIG. 1) would result in polypeptides devoid of C-terminal phosphatase catalytic domains, thereby leading to inactivation of the phosphatase. To evaluate whether tumor-specific point mutations alter phosphatase activity, we biochemically tested mutant versions of PTPRT, the most frequently mutated PTP in the superfamily. Mutations in both intracellular PTP domains (D1 and D2) were evaluated. His-tagged versions of the catalytic region of wild-type PTPRT, two D1 mutants (Q987K and N1128I), and three D2 mutants (R1212W, R1346L and T1368M) were produced in bacteria and analyzed for phosphatase activity using 6,8-difluoro-4-methylumbelliferyl phosphate (DiFMUP) as a substrate (FIG. 2) (12). All D1 and D2 mutants had reduced phosphatase activity compared with the wild-type protein (FIG. 2). Interestingly, the kinetic parameter $K_{cat}$ was reduced in both D1 mutants, while $K_m$ was increased in all three D2 mutants, suggesting that mutations in the two domains may have different effects on enzymatic activity. Although the D2 domain has been thought to usually be catalytically inactive (1), these results are consistent with recent studies that show that the D2 domain is important for phosphatase activity in some receptor phosphatases (15). These biochemical data on missense mutations, coupled with the large number of truncating mutations noted above, suggest that PTPRT functions as a tumor suppressor gene.

Example 5

Phosphatase Functions as Tumor Suppressor

Figure 3A:
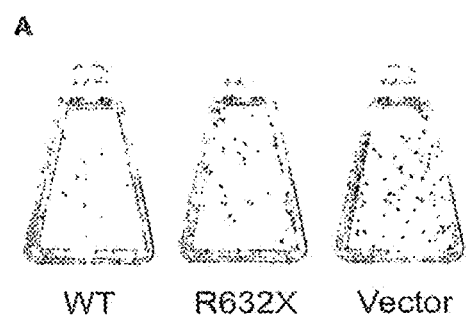
FIG. 3A-3B. PTPRT overexpression suppresses growth of human cancer cells.
Figure 3B:
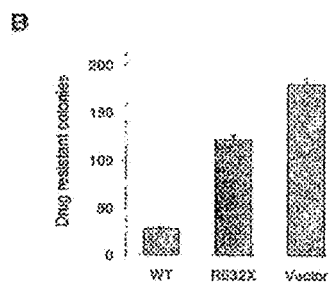

To determine whether PTPRT inhibits tumor cell growth, we transfected wild-type PTPRT into HCT116 colorectal cancer cells (12). An identical expression vector containing an R632X mutant of PTPRT was used for comparison. Wild-type PTPRT potently inhibited cell growth in this assay, as seen by the substantial decrease in the number of neomycin resistant colonies compared with the R632X mutant or with vector alone (FIGS. 3A, 3B). Similar results with wild-type and mutant PTPRT were also observed in DLD1 colorectal cancer cells.

Example 6

Discussion

The combination of these genetic, biochemical, and cellular data suggest that PTPRT and the other identified phosphatases are likely to act as tumor suppressors. This is consistent with the function of other phosphatases implicated in tumorigenesis (7,8,16), and with the general role of phosphatases in inhibiting various growth promoting signaling pathways (2). The absence of biallelic mutations in a subset of the analyzed tumors suggests that some alterations may act in a dominant negative fashion or may affect gene dosage, mechanisms that have been previously involved in inactivation of other tumor suppressor genes (17, 18).

Figure 4:
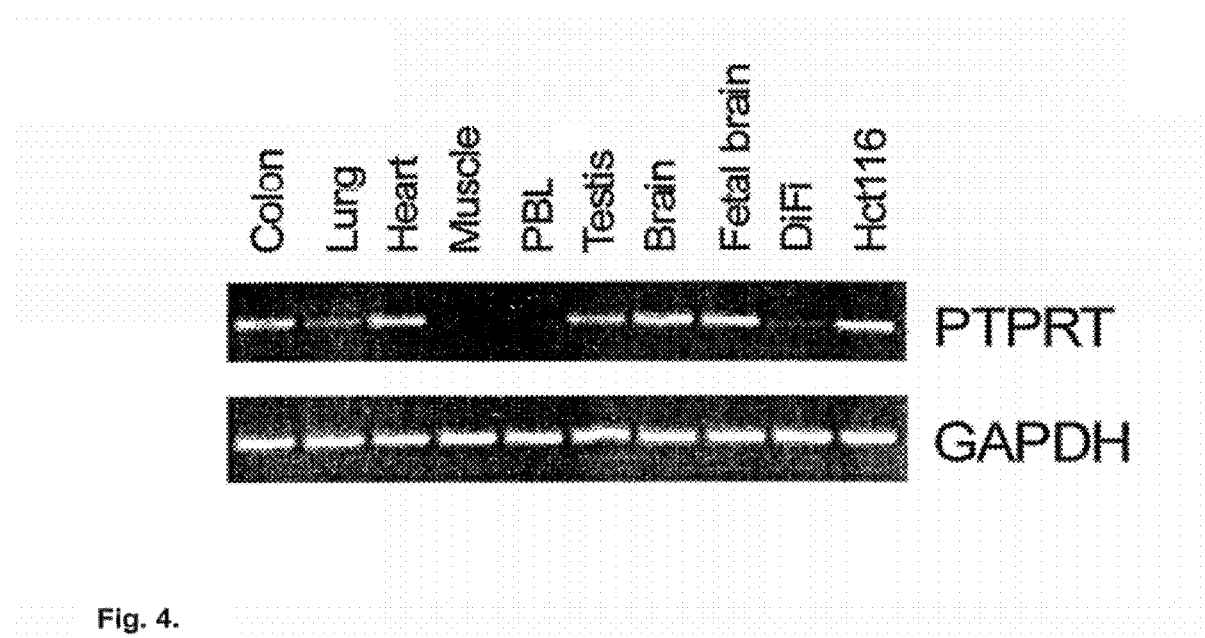
FIG. 4. Expression analysis of PTPRT. PTPRT expression was evaluated by reverse transcription of total RNA followed by PCR amplification using a forward primer from exon 31 and a reverse primer from exon 32. Expression analysis of glyceraldehyde-3-phosphate dehydrogenase (GAPDH) was performed as a control. Tissues analyzed are indicated above. PBL represents peripheral blood leukocytes; DiFi and Hct116 represent cancer cell lines derived from the colon.

Little is known about the functional role of the tyrosine phosphatases discussed here. PTPN13 appears to be involved in apoptosis (19) and may be partly responsible for the anti-tumor effects of tamoxifen (20). Overexpression of PTPN3 inhibits growth of NIH/3T3 cells, possibly through interaction with valosin containing protein (VCP/p97) (21). PTPN14 and PTPRF are thought to play a role in cell adhesion by regulating tyrosine phosphorylation of adherens junction proteins (22, 23). As increased phosphorylation of adherens junctions has been shown to increase cell motility and migration (22, 24), mutational inactivation of these genes may be an important step in cancer cell invasion and metastasis. PTPRG maps to chromosome 3p14.2, a region frequently lost in lung, renal and early stage breast tumors, and is thought to be a target of the translocation at 3p14 in familial renal cell carcinoma (25-27). However, no point mutations in PTPRG (28) or any of the other genes identified here have been previously described in any cancer. PTPRT is expressed in the developing central nervous system and in the adult cerebellum (29) and had not been thought to play a role in the growth or differentiation of other tissues. We have found that PTPRT is expressed in a variety of human tissues, including normal colon epithelium as well as cells derived from colorectal cancers (FIG. 4).

Example 7

Materials and Methods

Identification of PTP genes. Protein tyrosine phosphatase genes were identified by analysis of InterPro (IPR) phosphatase domains present within the Celera draft human genome sequence. IPR003595, IPR000340, IPR000751 and IPR002115 were used to search all known and predicted genes for classical PTPs (RPTPs and NRPTPs), DSPs, DSPs related to CDC25, and LMPs, respectively. This resulted in identification of 91 tyrosine phosphatases, three of which were pseudogenes and therefore not analyzed further. PTEN, which has been determined to act primarily as a lipid phosphatase was also not analyzed.

PCR, sequencing, and mutational analysis. Sequences for all available annotated exons and adjacent intronic sequences of identified PTP, DSP and LMP genes were extracted from Celera draft human genome sequence (website: celera.com) or from GenBank (website: genbank.nlm.nih.gov). Celera and public accession numbers of all analyzed genes are available in FIG. 6 (Table S2).

Primers for PCR amplification and sequencing were designed using the Primer 3 program (available from a Massachusetts Institute of Technology (MIT) website), and were synthesized by MWG (High Point, N.C.) or IDT (Coralville, Iowa). PCR amplification and sequencing were performed on tumor DNA from 18 early passage cell lines as previously described (6) using a 384 capillary automated sequencing apparatus (Spectrumedix, State College, Pa.). Sequence traces were assembled and analyzed to identify potential genomic alterations using the Mutation Explorer software package (SoftGenetics, State College, Pa.). Of the 1375 exons extracted, 92% were successfully analyzed, each in an average of 17 tumor samples. All mutations listed in Table 51 were determined to be somatic except in 10 cases in which no normal tissue was available for comparison.

Construction of wild-type and mutant PTPRT proteins. The region encoding two catalytic domains of PTPRT was cloned by PCR using Platinum Hi-fidelity Taq polymerase (Invitrogen, Carlsbad, Calif.) from human fetal brain cDNA with primers GGAATTCCATATGGCCTTACCA-GAGGGGCAGACAG (SEQ ID NO: 1) and CGGGATC-CCCCAGTTACTGCCATTCACA (SEQ ID NO: 2) and cloned in frame fused to the 6× His tag of pET19b expression vector (Novagen, Madison, Wis.). The Q987K, N1128I, R1212W, R1346L and T1368M mutants were made using sexual PCR (Ref 30). The primers CAAAAGTCCTTTA-CAGTCTCCTTCATCGGACCTTGAGTCGCAATG (SEQ ID NO: 3) and AAGGAGACTGTAAAGGACTTTTGGAG (SEQ ID NO: 4) were used as mutagenic primers for the Q987K mutant; the primers CCATGCTTGACATGGC-CGAGATTGAAGGGGTGGTGGACATCTTC (SEQ ID NO: 5) and ATCTCGGCCATGTCAAGCATGG (SEQ ID NO:6) were used as mutagenic primers for the N1128I mutant; the primers CAATGCTGCAGTCCTCGGGCCA-CACACGGGGTGTCACAATG (SEQ ID NO: 7) and TGGCCCGAGGACTGCAGCATTG (SEQ ID NO: 8) were used as mutagenic primers for the R1212W mutant; the primers CTATACGATAACCATCCTGTGGCAGGGC-CATGTTACAGATGCG (SEQ ID NO: 9) and TGCCACAG-GATGGTTATCGTATAG (SEQ ID NO: 10) were used as mutagenic primers for the R1346L mutant; and the primers GAGCGCTTGGAGGGGGGCATGTCCCGG-TAGGCAGGCC (SEQ ID NO: 11) and TGCCCCCCTC-CAAGCGCTC (SEQ ID NO: 12) were used as mutagenic primers for the T1368M mutant. For expression of recombinant proteins, BL21-DE3 bacteria were grown to late log phase and induced with 1 mM IPTG for 3 hours at 37° C. Bacterial lysates were made by sonication in lysis buffer (1 mM Tris, 1 M NaCl, 10 mM imidazole 0.1% igepal, pH 8.0) and incubated with Ni-NTA beads for 45 min at 4° C. The Ni-NTA beads were washed with 50 mM imidazole buffer (40 mM Tris, 100 mM NaCl, 50 mM imidazole, pH8.0) and bound protein was eluted with 500 mM imidazole.

Phosphatase kinetic analysis. Various concentrations of 6,8-difluoro-4-methylumbelliferyl phosphate (DiFMUP—Molecular Probes D6567) were incubated with 800 ng of purified protein in 40 mM Tris-HCl pH8.0, 100 mM NaCl, 5 mM CaCl2, and 10 mM DTT in a 100 uL reaction. The reaction was incubated at 37° C. for 30 minutes and fluorometric measurements were taken at an excitation wavelength of 360 nm and an emission wavelength of 460 nm and extrapolated to a standard curve of 6,8-difluoro-4-methylumbelliferone. The data were fitted to the Michaelis-Menton equation using GraphPad Prism v. 3.02.

Cell proliferation assays. Full length wild-type or R632X mutant PTPRT cDNA sequences were cloned into the pCI-Neo vector (Promega, Madison, Wis.). Subconfluent HCT116 and DLD1 colorectal cancer cells were transfected with equal amounts of the wild-type PTPRT construct, R632X mutant PTPRT construct, or empty vector and grown for 48 hours. Cells were then trypsinized and plated in T25 flasks with fresh media containing geneticin. Cells were grown for 2-3 weeks and stained with crystal violet. The expression level and the mutational status of PTPRT are not known in either HCT116 or DLD1 cells as no normal tissues from the same patients are available as controls.

Expression analysis. Total RNAs from various human tissues were purchased form BD Bioscience (San Jose, Calif.) and equal amounts were reverse transcribed into cDNAs with random primers. PTPRT expression was examined by PCR using primers CCACATCGTGAAAACACTGC (SEQ ID NO: 13) and CAACAGGAGACCCCTCAGAA (SEQ ID NO: 14) which are located in exons 31 and 32 and result in a 284 bp product.

REFERENCES

The disclosure of each reference cited is expressly incorporated herein.
1. B. G. Neel, N. K. Tonks, Curr. Opin. Cell Biol. 9, 193 (1997).
2. T. Hunter, Philos. Trans. R. Soc. Lond. B. Biol. Sci. 353, 583 (1998).
3. P. Blume-Jensen, T. Hunter, Nature 411, 355 (2001).
4. H. Davies et al., Nature 417, 949 (2002).
5. H. Rajagopalan et al., Nature 418, 934 (2002).
6. A. Bardelli et al., Science 300, 949 (2003).
7. J. Li et al., Science 275, 1943 (1997).
8. P. A. Steck et al., Nat. Genet 15, 356 (1997).
9. M. Tartaglia et al., Nat. Genet 34, 148 (2003).
10. S. Saha et al., Science 294, 1343 (2001).
11. A. R. Forrest et al., Genome Res. 13, 1443 (2003).
12. Materials and Methods are available as Supporting Online Material.
13. J. N. Andersen et al., Mol. Cell. Biol. 21, 7117 (2001).
14. T. L. Wang et al., Proc. Natl. Acad. Sci. USA 99, 3076 (2002).
15. A. Organesian et al., Proc. Natl. Acad. Sci. USA 100, 7563 (2003)
16. S. S. Wang et al., Science 282, 284 (1998).
17. S. E. Kern et al., Science 256, 827 (1992).
18. R. Fodde, R. Smits, Science 298, 761 (2002).
19. G. Bompard, C. Puech, C. Prebois, F. Vignon, G. Freiss, J. Biol. Chem. 277, 47861 (2002).
20. G. Freiss, C. Puech, F. Vignon, Mol. Endocrinol. 12, 568 (1998).
21. S. H. Zhang, J. Liu, R. Kobayashi, N. K. Tonks, J. Biol. Chem. 274, 17806 (1999).
22. C. Wadham, J. R. Gamble, M. A. Vadas, Y. Khew-Goodall, Mol. Biol. Cell. 14, 2520 (2003).
23. T. Muller, A. Choidas, E. Reichmann, A. Ullrich, J. Biol. Chem. 274, 10173 (1999).
24. O. Ayalon, B. Geiger, J. Cell. Sci. 110, 547 (1997).
25. S. LaForgia et al., Proc. Natl. Acad. Sci. USA 88, 5036 (1991).
26. I. Panagopoulos et al., Cancer Res. 56, 4871 (1996).
27. K. Kastury et al., Genomics 32, 225 (1996).
28. T. Druck et al., Cancer Res. 55, 5348 (1995).
29. P. E. McAndrew et al., J. Comp. Neurol. 391, 444 (1998).
30. R. Higuchi, B. Krummel, R. K. Saiki, Nucleic Acids Res. 16, 7351 (1988).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09012145B2). An electronic copy of the "Sequence Listing" will also be available from the USPTO upon request and payment of the fee set forth in 37 CFR 1.19(b)(3).

We claim:

1. A method of categorizing human cancers selected from the group consisting of lung, colorectal, and gastric cancer tissues, comprising:
   determining the coding sequence for protein tyrosine phosphatase family member PTPRT in a sample of a cancer tissue selected from the group consisting of lung, colorectal, and gastric cancer tissues;
   identifying a somatic mutation of said protein tyrosine phosphatase family member in the cancer tissue;
   assigning the cancer tissue to a group based on the presence or absence of the somatic mutation.

2. The method of claim 1 wherein the mutation is one which truncates the protein tyrosine phosphatase family member.

3. The method of claim 1 wherein the mutation is non-synonymous.

4. The method of claim 1 wherein the mutation is a point mutation.

5. The method of claim 1 wherein the group is used to identify cancer.

6. The method of claim 1 wherein the cancer tissue is colorectal.

7. The method of claim 1 wherein the cancer tissue is lung.

8. The method of claim 1 wherein the cancer tissue is gastric.

9. A method of testing a sample collected from a human, comprising:
   determining the coding sequence for protein tyrosine phosphatase family member PTPRT in the sample collected from the human, wherein the sample is selected from the group consisting of:
   a suspected colorectal cancer tissue,
   a suspected gastric cancer tissue,
   a suspected lung cancer tissue, and
   blood, serum, plasma, or stool of a human who has a colorectal, gastric, or lung cancer;
   identifying a somatic mutation of said protein tyrosine phosphatase family members in the sample, wherein the somatic mutation diminishes the expression and/or enzymatic function of PTPRT.

10. The method of claim 9 wherein the sample is selected from the group consisting of a suspected colorectal cancer tissue, a suspected gastric cancer tissue, a suspected lung cancer tissue, blood, and stool.

11. The method of claim 1 wherein the somatic mutation diminishes the expression and/or enzymatic function of PTPRT.

12. The method of claim 1 wherein the step of determining the coding sequence is performed using primers.

13. The method of claim 9 wherein the step of determining the coding sequence is performed using primers.

14. The method of claim 1 wherein the step of determining the coding sequence employs DNA amplification.

15. The method of claim 9 wherein the step of determining the coding sequence employs DNA amplification.

16. The method of claim 1 wherein the step of determining the coding sequence employs dye terminators.

17. The method of claim 9 wherein the step of determining the coding sequence employs dye terminators.

18. The method of claim 1 wherein the step of determining the coding sequence is performed on genomic DNA.

19. The method of claim 9 wherein the step of determining the coding sequence is performed on genomic DNA.

20. The method of claim 1 wherein the step of determining the coding sequence is performed on amplified exons.

21. The method of claim 9 wherein the step of determining the coding sequence is performed on amplified exons.

* * * * *